United States Patent
Deubel

(10) Patent No.: US 10,100,067 B2
(45) Date of Patent: Oct. 16, 2018

(54) METHOD FOR PRODUCING CYANOALKYL FLUOROSILANES

(71) Applicant: Wacker Chemie AG, Munich (DE)

(72) Inventor: Frank Deubel, Erding (DE)

(73) Assignee: WACKER CHEMIE AG, Munich (DE)

( * ) Notice: Subject to any disclaimer, the term of this patent is extended or adjusted under 35 U.S.C. 154(b) by 0 days.

(21) Appl. No.: 15/547,634

(22) PCT Filed: Nov. 2, 2016

(86) PCT No.: PCT/EP2016/076367
§ 371 (c)(1),
(2) Date: Jul. 31, 2017

(87) PCT Pub. No.: WO2017/080878
PCT Pub. Date: May 18, 2017

(65) Prior Publication Data
US 2018/0258108 A1    Sep. 13, 2018

(30) Foreign Application Priority Data
Nov. 9, 2015    (DE) .................. 10 2015 222 019

(51) Int. Cl.
*C07F 7/12*    (2006.01)
*C07B 39/00*    (2006.01)

(52) U.S. Cl.
CPC .............. *C07F 7/123* (2013.01); *C07B 39/00* (2013.01)

(58) Field of Classification Search
CPC .................................. C07F 7/123; C07B 39/00
See application file for complete search history.

(56) References Cited

U.S. PATENT DOCUMENTS

2014/0356735 A1    12/2014    Pena Hueso et al.

FOREIGN PATENT DOCUMENTS

| EP | 0599278 B1 | 1/1996 |
|---|---|---|
| JP | 56167693 A | 12/1981 |
| JP | 0680678 A | 3/1994 |
| JP | 11012287 A | 1/1999 |
| WO | 2014197609 A2 | 12/2014 |

OTHER PUBLICATIONS

Young-Soo Kim, Hochun Lee and Hyun-Kon Song: "Surface Complex Formation between Aliphatic Nitrile Molecules and Transition Metal Atoms for Thermally Stable Lithium-Ion Batteries", ACS Appl. Mater. Interfaces, 2014, 6 (11), pp. 3913-8920.
A. E. Newkirk: J. Am. Chem. Soc., 1946, vol. 68 (12), pp. 2736-2737.

*Primary Examiner* — Jafar F Parsa
(74) *Attorney, Agent, or Firm* — Brooks Kushman P.C.

(57) ABSTRACT

Cyanoalkylfluorosilanes are prepared in exceptionally high yield by the reaction of the corresponding cyanoalkylchlorosilanes with specific metal fluorides. The products are useful in lithium ion battery electrolyte composition.

11 Claims, No Drawings

METHOD FOR PRODUCING CYANOALKYL FLUOROSILANES

CROSS REFERENCE TO RELATED APPLICATIONS

This application is the U.S. National Phase of PCT Appln. No. PCT/EP2016/076367 filed Nov. 2, 2016, which claims priority to German Application No. 10 2015 222 019.2 filed Nov. 9, 2015, the disclosures of which are incorporated in their entirety by reference herein.

BACKGROUND OF THE INVENTION

1. Field of the Invention

The invention relates to a process for preparing cyanoalkylfluorosilanes by reacting cyanoalkylchlorosilanes with metal fluoride.

2. Description of the Related Art

The development of more powerful lithium-ion cells also continually requires new electrolyte materials in order to meet the new requirements that emerge. New components are frequently added to the base electrolyte for the purpose, for example, of protection against overcharging, for a more stable SEI or else for the thermal stabilization of the electrolyte. For electrolytes with particular thermal stability, for example, organic cyanides are used, as described for example in "Surface Complex Formation between Aliphatic Nitrile Molecules and Transition Metal Atoms for Thermally Stable Lithium-Ion Batteries" (Young-Soo Kim, Hochun Lee and Hyun-Kon Song; ACS Appl. Mater. Interfaces, 2014, 6 (11), pp 8913-8920). The solutions of $LiPF_6$ as conducting salt in fluorosilanes containing cyano groups are also described in U.S. 2014/0356735 A1 as being of particularly high thermal stability. As a result, the evolution of gas which is frequently observed when lithium-ion cells experience thermal loading, and which is caused by decomposition of the electrolyte, can be reduced significantly.

US 2014/0356735 A1 describes the preparation of 3-cyanopropyldimethylfluorosilane by reaction of 3-cyanopropyldimethylchlorosilane with ammonium bifluoride. Because of its corrosiveness, however, ammonium bifluoride is not suitable for use in metal containers or glass apparatus. Moreover, gaseous hydrogen chloride is formed stoichiometrically during the reaction. The resultant ammonium salts, furthermore, cause problems on subsequent workup. An alternative fluorination with KF and/or NaF is slow and necessitates the use of solvents which have to be separated from the reaction product, such separation being costly and inconvenient.

The preparation of cyanoalkyl-functional fluorosilanes such as 3-cyanopropyldimethylfluorosilane, for example, as known from US 2014/0356735 A1, by fluorination of 3-cyanopropyldimethylchlorosilane using ammonium bifluoride, is therefore difficult to implement on an industrial scale.

Zinc fluoride as a fluorinating agent for the halogen exchange on hydridochlorosilanes in the presence of solvents is known in principle from EP 0599278 B1, but achieves conversions of below 90% at most. The solvent-free preparation of organofluorosilanes with $ZnF_2$ leads only to yields <50% (A.E. Newkirk, J. Am. Chem. Soc., 1946, 68 (12), pp 2736-2737).

SUMMARY OF THE INVENTION

It was an object of the present invention to provide a process for preparing cyanoalkylfluorosilanes that avoids corrosive byproducts and leads in industrial implementation to high yields with high purity. These and other objects are surprisingly and unexpectedly achieved by a process for preparing cyanoalkylfluorosilanes of the general formula I

$$N\equiv C-(CH_2)_n-SiF_{3-x}R_x \qquad (I),$$

wherein cyanoalkylchlorosilanes of the general formula II

$$N\equiv C-(CH_2)_n-SiCl_{3-x}R_x \qquad (II),$$

are reacted with metal fluoride, wherein the metal is selected from main group 1 and from the lightest metals of transition groups 8, 1B, and 2B of the periodic table of the elements,
R denotes an alkyl radical,
n denotes integral values from 1 to 10, and
x denotes the values 0, 1 or 2.

DETAILED DESCRIPTION OF THE PREFERRED EMBODIMENTS

In the process of the invention it has been possible, surprisingly, to find a fluorination with or without solvent that operates quickly, quantitatively, and without problematic byproducts, in particular without formation of corrosive HCl. Furthermore, the workup of the reaction mixture is facilitated considerably through avoidance of ammonium salts.

Examples of the alkyl radicals R are the methyl, ethyl, n-propyl, isopropyl, 1-n-butyl, 2-n-butyl, isobutyl, tert-butyl, n-pentyl, isopentyl, neopentyl, and tert-pentyl radicals; hexyl radicals such as the n-hexyl radical; heptyl radicals such as the n-heptyl radical; octyl radicals such as the n-octyl radical, isooctyl radicals and the 2,2,4-trimethylpentyl radical; nonyl radicals such as the n-nonyl radical; decyl radicals such as the n-decyl radical; dodecyl radicals such as the n-dodecyl radical; octadecyl radicals, such as the n-octadecyl radical; and cycloalkyl radicals such as the cyclopentyl, cyclohexyl, cycloheptyl and methylcyclohexyl radicals.

Preferred radicals R are alkyl radicals, more preferably linear alkyl radicals having 1 to 6 carbon atoms. Greater preference is given to the methyl, ethyl, n-propyl, and isopropyl radicals.

Preferably n denotes integral values from 1 to 6, and more preferably the values 3 and 4.

Preferably x denotes the value 2.

In particular, 3-cyanopropyldimethylchlorosilane is used and 3-cyanopropyldimethylfluorosilane is prepared.

In the process it is possible to use a metal fluoride of a single metal, a mixed fluoride of two or more metals, or a mixture of two or more metal fluorides selected from metal fluorides of a single metal and mixed fluorides of two or more metals.

Preferred are the fluorides of the metals Li, Na, K, Rb, Cs, Fe, Co, Ni, Cu and Zn. Particularly preferred are $ZnF_2$ and the mixed fluoride of Zn and K.

$ZnF_2$ and $KZnF_3$ are particularly preferred, since they are particularly reactive, are not hygroscopic, and give rise to relatively little toxicological concern.

With preference, 1.00 mol to 2 mol of fluoride, more preferably 1.05 mol to 1.5 mol of fluoride, more particularly 1.1 mol to 1.3 mol of fluoride are used per mole of chlorine in the cyanoalkylchlorosilane.

The reaction can be carried out in bulk, in other words without solvent. In that case, preferably, the cyanoalkylchlorosilane is introduced first and the metal fluoride is added.

The reaction can also be carried out in solution. In that case, preferably, the metal fluoride in solvent is introduced first, and the cyanoalkylchlorosilane is added in pure form or as a solution.

Solvents can be used, preferably in amounts of at least 1% and at most 200%, more preferably at least 10% and at most 100%, based on the reaction mixture. Examples of solvents are aprotic solvents, preferably linear or cyclic, saturated or unsaturated hydrocarbons, e.g., pentane, cyclohexane, toluene, ethers such as methyl Cert-butyl ether, anisole, tetrahydrofuran or dioxane, halogenated hydrocarbons, such as dichloromethane, 1,2-dichloroethane or chlorobenzene, nitriles such as acetonitrile or propionitrile or DMSO.

The reaction is preferably carried out at temperatures of 0 to 180° C., more preferably of 20 to 150° C., preferably under pressures of from 100 mbar to 10 bar, more preferably from 800 mbar to 2 bar.

The reaction times are preferably 1 min to 8 hours, more preferably 10 min to 4 hours.

All above symbols in the above formulae have their definitions in each case independently of one another. In all formulae the silicon atom is tetravalent. The sum of all the constituents of the reaction mixture makes 100 wt %.

In the following examples, unless indicated otherwise in each case, all quantity and percentage figures are given by weight and all pressures are 0.10 MPa (abs.).

Unless otherwise indicated, the examples below were carried out at room temperature, in other words at 23° C. The solvents used for the syntheses were dried by standard methods and kept under a dry argon atmosphere.

The following materials were acquired from commercial sources and used directly without further purification: zinc fluoride, anhydrous (Sigma-Aldrich), potassium fluoride (Sigma-Aldrich), acetonitrile, anhydrous (Sigma-Aldrich), zinc chloride (Sigma-Aldrich).

Example 1: Fluorination with Zinc Fluoride in Acetonitrile 5.0 g 3-cyanopropyldimethylchlorosilane
1.6 g zinc fluoride, dry
10 ml acetonitrile, dry Procedure: The acetonitrile and the zinc fluoride are charged under nitrogen to a 50 ml two-neck flask. This initial charge is heated to 75° C. and the 3-cyanopropyldimethylchlorosilane is added dropwise with stirring.

This is followed by stirring at 75° C. for 4 h.

There is complete conversion of the chlorosilane to the desired 3-cyanopropyldimethylfluorosilane.

Example 2: Fluorination with Zinc Fluoride in Bulk 165 g 3-cyanopropyldimethylchlorosilane
68 g zinc fluoride, anhydrous Apparatus: 1000 ml three-neck flask with coil condenser, thermometer Procedure: 3-cyanopropyldimethylchlorosilane is introduced initially and the zinc fluoride is added in portions with stirring. The reaction material heats up to 104° C., and is subsequently stirred at 70° C. for one hour.

There is complete fluorination of the 3-cyanopropyldimethylchlorosilane to 3-cyanopropyldimethylfluorosilane.

Example 3: Preparation of Potassium Zinc Fluoride 10 g zinc chloride (73 mmol)
12.8 g potassium fluoride
50 ml water Apparatus: 100 ml three-neck flask with thermometer, reflux condenser, and 25 ml dropping funnel The potassium fluoride is introduced into the flask together with 40 ml of water and this initial charge is heated to 50° C.

The zinc chloride is dissolved in a glass beaker together with 10 ml of water, and the resulting zinc chloride solution is added slowly dropwise from the dropping funnel at 50° C., the product being formed as a white precipitate.

Following complete addition, the stirring is continued for 5 hours more at room temperature.

Precipitate is filtered off with suction, dried initially at 100° C. and full vacuum, dried overnight at 180° C. and full vacuum, and then used as a fluorinating agent.

Final mass: 11.3 g (95% of theory)
24.6% K; 38% Zn; 36% F; 0.9% Cl; 0.1% H; 1.32% O Example 4: Fluorination with Potassium Zinc Fluoride in Bulk 4 g 3-cyanopropyldimethylchlorosilane
1.33 g zinc fluoride, anhydrous Apparatus: 25 ml two-neck flask with reflux condenser Procedure: The 3-cyanopropyldimethylchlorosilane is heated to 80° C. in the flask. $KZnF_3$ is added in portions with stirring. After the end of the addition, the batch is stirred for a further 2 h at 80° C.

Conversion: 94% based on the chlorosilane used.

The invention claimed is:

1. A process for preparing cyanoalkylfluorosilanes of the formula I $$N\equiv C-(CH_2)_n-SiF_{3-x}R_x \quad (I),$$

comprising reacting cyanoalkylchlorosilanes of the formula II $$N\equiv C-(CH_2)_n-SiCl_{3-x}R_x \quad (II),$$

with metal fluoride, wherein the metal of the metal fluoride is selected from main group 1 and from the lightest metals of transition groups 8, 1B, and 2B of the periodic table of the elements,
R is an alkyl radical,
n is an integral value from 1 to 10, and
x is 0, 1 or 2.

2. The process of claim 1, wherein R is an alkyl radical having 1 to 6 carbon atoms.

3. The process of claim 1, wherein n is 3, 4 or 5.

4. The process of claim 2, wherein n is 3, 4 or 5.

5. The process of claim 1, wherein x is 2.

6. The process of claim 2, wherein x is 2.

7. The process of claim 3 wherein x is 2.

8. The process of claim 1, wherein 3-cyanopropyldimethylchlorosilane is used as a reactant and 3-cyanopropyldimethylfluorosilane is prepared as a product.

9. The process of claim 1, wherein the metal fluoride is $ZnF_2$ or a mixed fluoride of Zn and K.

10. The process of claim 1, wherein 1.00 mol to 2 mol of fluoride are used per mole of chlorine in the cyanoalkylchlorosilane.

11. The process of claim 1, wherein the reaction is carried out in bulk.

* * * * *